US012653942B2

(12) United States Patent
  Wall et al.

(10) Patent No.: US 12,653,942 B2
(45) Date of Patent: *Jun. 16, 2026

(54) MULTI-MODAL WOUND TREATMENT APPARATUS

(71) Applicant: Phase One Health, LLC, Nashville, TN (US)

(72) Inventors: Billy Wall, Arrington, TN (US); Stephen Galbraith, Franklin, TN (US); Robert Porter, Franklin, TN (US)

(73) Assignee: Phase One Health, LLC, Nashville, TN (US)

( * ) Notice: Subject to any disclaimer, the term of this patent is extended or adjusted under 35 U.S.C. 154(b) by 640 days.

This patent is subject to a terminal disclaimer.

(21) Appl. No.: 17/864,153

(22) Filed: Jul. 13, 2022

(65) Prior Publication Data

US 2023/0181813 A1     Jun. 15, 2023

Related U.S. Application Data

(63) Continuation of application No. 16/154,893, filed on Oct. 9, 2018, now Pat. No. 11,406,749, which is a
(Continued)

(51) Int. Cl.
  A61M 1/00      (2006.01)
  A61F 13/00     (2024.01)
  (Continued)

(52) U.S. Cl.
  CPC ............... A61M 1/85 (2021.05); A61F 13/05 (2024.01); A61L 2/202 (2013.01); A61M 1/74 (2021.05);
  (Continued)

(58) Field of Classification Search
  CPC .............. A61M 1/0023; A61M 1/0025; A61M 1/0027; A61M 1/0029; A61M 1/0031;
  (Continued)

(56) References Cited

U.S. PATENT DOCUMENTS 4,218,610 A     8/1980  Baxter et al.
5,069,880 A  *  12/1991 Karlson ..................... C02F 1/78
                                                422/186.07
(Continued)

FOREIGN PATENT DOCUMENTS

EP        1100574      5/2001
KR      101123897      4/2012
(Continued)

*Primary Examiner* — James D Ponton
(74) *Attorney, Agent, or Firm* — Jacob W. Neu; Bradley Arant Boult Cummings LLP

(57) ABSTRACT

The wound treatment apparatus combines an internal negative pressure (vacuum) pump and an internal positive pressure (compressor) pump connectable to an external oxygen supply for providing both negative pressure wound therapy and hyperbaric oxygen wound therapy to a wound site. The apparatus also includes a user interface operatively connected to an electronic controller that monitors and actuates the vacuum and compressor pumps. The user interface and controller enables the apparatus to provide multiple modes of operation and the ability to selectively change between negative pressure therapy operational modes and hyperbaric oxygen operational modes.

3 Claims, 6 Drawing Sheets

Related U.S. Application Data continuation of application No. 14/378,306, filed as application No. PCT/US2013/025901 on Feb. 13, 2013, now Pat. No. 10,117,975.

(60) Provisional application No. 61/633,515, filed on Feb. 13, 2012, provisional application No. 61/633,527, filed on Feb. 13, 2012, provisional application No. 61/633,516, filed on Feb. 13, 2012, provisional application No. 61/633,517, filed on Feb. 13, 2012, provisional application No. 61/633,528, filed on Feb. 13, 2012, provisional application No. 61/633,529, filed on Feb. 13, 2012.

(51) Int. Cl.

| | |
|---|---|
| *A61F 13/05* | (2024.01) |
| *A61L 2/20* | (2006.01) |
| *A61L 2/202* | (2026.01) |
| *A61M 35/00* | (2006.01) |

(52) U.S. Cl.
CPC ................ *A61M 1/94* (2021.05); *A61M 1/95* (2021.05); *A61M 1/96* (2021.05); *A61M 1/962* (2021.05); *A61M 35/30* (2019.05); *A61F 2013/0028* (2013.01); *A61M 1/75* (2021.05); *A61M 35/25* (2019.05); *A61M 2202/0208* (2013.01); *A61M 2202/0216* (2013.01); *A61M 2205/05* (2013.01); *A61M 2205/3331* (2013.01); *A61M 2209/10* (2013.01); *A61M 2230/00* (2013.01)

(58) Field of Classification Search
CPC .............. A61M 1/0035; A61M 1/0066; A61M 1/0084; A61M 1/0058; A61M 1/0062; A61M 27/00; A61F 13/00068; A61F 13/0216

See application file for complete search history.

(56) References Cited

U.S. PATENT DOCUMENTS

| | | | | |
|---|---|---|---|---|
| 7,524,315 | B2 | 4/2009 | Blott et al. | |
| 7,648,488 | B2 | 1/2010 | Smith et al. | |
| 8,011,039 | B2 | 9/2011 | Stryker et al. | |
| 8,021,348 | B2 * | 9/2011 | Risk, Jr. .................. | A61M 1/92 604/319 |
| 8,100,956 | B2 * | 1/2012 | Quisenberry ........... | A61F 13/05 604/23 |
| 8,128,672 | B2 | 3/2012 | Quisenberry et al. | |
| 8,273,074 | B2 | 9/2012 | Jaeb et al. | |
| 8,273,855 | B2 | 9/2012 | Xiao | |
| 8,357,130 | B2 | 1/2013 | Smith et al. | |
| 8,425,580 | B2 | 4/2013 | Quisenberry et al. | |
| 10,117,975 | B2 * | 11/2018 | Wall ......................... | A61M 1/96 |
| 11,406,749 | B2 * | 8/2022 | Wall ......................... | A61F 13/05 |
| 2007/0118096 | A1 * | 5/2007 | Smith ..................... | A61M 1/94 604/541 |
| 2007/0260226 | A1 * | 11/2007 | Jaeb ........................ | A61M 1/74 604/543 |
| 2009/0293879 | A1 | 12/2009 | Frånberg et al. | |
| 2010/0030132 | A1 * | 2/2010 | Niezgoda ................ | A61M 1/73 604/289 |
| 2010/0150991 | A1 | 6/2010 | Bernstein | |

FOREIGN PATENT DOCUMENTS

| | | |
|---|---|---|
| WO | 2006119473 | 11/2006 |
| WO | 2007062024 | 5/2007 |
| WO | 2008130689 | 10/2008 |

* cited by examiner

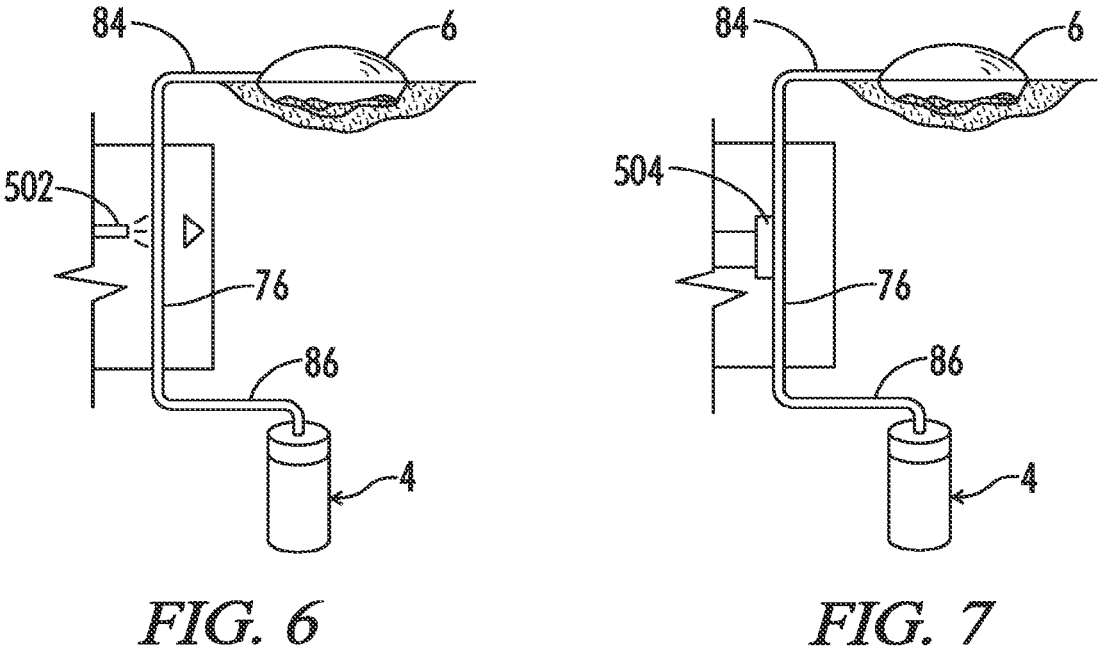
*FIG. 6*                                    *FIG. 7*
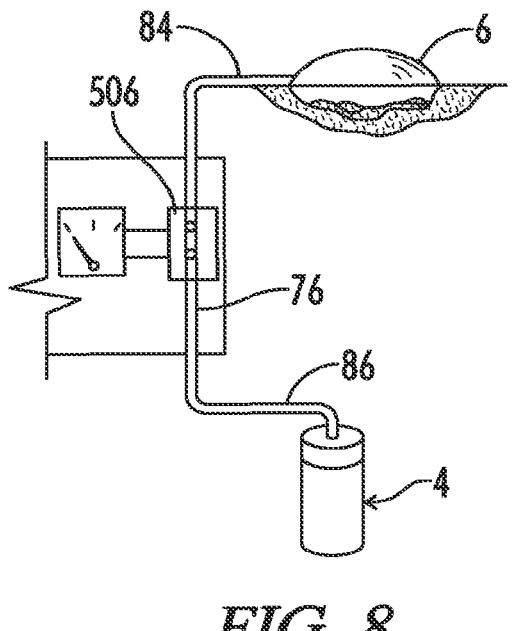
*FIG. 8*

MULTI-MODAL WOUND TREATMENT APPARATUS

TECHNICAL FIELD

The present invention relates to methods and systems for providing therapeutic treatment of chronic and acute wounds. More particularly, the present invention pertains to devices and methods for delivering multi-modal treatment therapies to a wound site.

BACKGROUND ART

Chronic and acute wounds, including pressure ulcers, diabetic wounds, and burns, present significant challenges to the health care industry. Patient care providers are actively seeking methods, devices, and systems for treating such wounds at a lower cost and with greater efficacy.

Conventional treatments for chronic wounds typically include either negative pressure therapy and/or hyperbaric oxygen therapy.

Negative pressure therapy is the controlled application of sub-atmospheric pressure to a wound using a therapy unit, such as a vacuum or suction device, to expose the wound to negative pressure to help promote wound healing. The wound is typically covered to facilitate the application of negative pressure and suction at the wound area. Various types of resilient, open cell foam surface dressings are typically sealed within an adhesive drape to provide the sub-atmospheric pressure at the wound site. Exudates are drained from the wound site and typically directed to a canister that stores the fluids and/or infectious material until properly disposed. Negative pressure wound therapy is often prescribed for chronic and acute wound types such as diabetic wounds, pressure ulcers, abdominal wounds, trauma wounds, various burns, flaps and grafts. However, negative pressure therapy may be less effective on patients having vascular disorders, such as diabetes, because negative pressure therapy can create a hypoxic environment at the wound. In current hospital settings, portable vacuum pumps are often rented or purchased for the purpose of providing negative pressure therapy. This can significantly increase the cumulative costs of providing wound care.

Hyperbaric oxygen therapy is the controlled application of oxygen to a wound at greater-than-atmospheric pressures. Oxygen is typically required for all new cell growth. Chronic or non-healing wounds tend to exhibit low oxygen tensions, or tend to be ischemic. A wound can become dormant if the amount of poorly oxygenated wound tissue reaches a critical mass. In this state, the body may no longer recognize the need to heal the affected area, thereby exacerbating the lack of oxygen in the wound and impairing healing of the wound by the body. Oxygen therapy is particularly useful for patients with poor circulation. The oxygen helps to kill bacteria and when applied to an open wound at a hyperbaric level, the oxygen is dissolved into the wound and absorbed by the surface wound tissue. The cells of the wound tissue that absorb the oxygen will begin metabolic activity in response to the increased oxygen tension. When the oxygen source is removed, the previously active cells request more oxygen from the body. The body responds by beginning to form new blood cells, and thus, starting the healing process. Accordingly, when delivered to a wound site under hyperbaric conditions, oxygen may act as a primary wound treatment fluid Typically, hyperbaric oxygen therapy is delivered by placing the patient in a hyperbaric chamber that encompasses the full body of the patient or an entire extremity, such as a leg or an arm. Such chambers are problematic due to their lack of portability, the difficulty in sterilization of the chambers between patients, and the potential adverse effects of breathing oxygen at hyperbaric pressure. Preferably, hyperbaric oxygen treatment should be localized at the wound site rather than applied to the patient's entire body or extremity.

While both negative pressure and hyperbaric oxygen therapies are each believed to be effective when administered as separate wound care treatments, many patients may benefit from a treatment protocol incorporating both negative pressure and hyperbaric oxygen therapies. Because existing hyperbaric oxygen treatment is typically performed in a hyperbaric chamber, switching between negative pressure therapy and hyperbaric oxygen therapy is time-consuming. Before entering a hyperbaric oxygen chamber, a patient must first be disconnected from the negative therapy device. The negative pressure therapy dressing, which typically includes packing materials, a drain, tubing, and sealing material, must then be removed. Following hyperbaric oxygen treatment, a new negative pressure dressing would have to be applied. These procedures are wasteful and time-consuming, making it difficult, if not impossible, to alternate between negative pressure therapy and hyperbaric oxygen therapy every few minutes or less.

More recently, wound care systems and methods have been developed that combine negative and positive pressure (e.g. hyperbaric oxygen) wound treatment therapies. Such methods and systems are described, for example, in U.S. Pat. No. 7,648,488 issued Jan. 19, 2010; U.S. Pat. No. 8,357,130 issued Jan. 22, 2013; U.S. Patent Publication No. 2008/0140029; and U.S. Patent Publication No. 2010/0121287; all of which are hereby incorporated in their entirety by reference.

Wound care treatment may be further enhanced by deactivating pathogenic microorganisms within the wound environment and physically removing the deactivated microorganisms and other toxins from the wound site. While antibiotics and other drugs may be effective in destroying bacteria and other pathogens, their activity may disrupt the cell walls of the microorganisms, thereby releasing harmful enzymes and other toxins into the wound environment. These harmful enzymes and toxins must be removed or they may become cytotoxic.

It is also known that when planktonic, free floating, individual microorganisms, like bacteria, attach to a surface and gather in groups within a wound environment, they may produce an extra-cellular matrix called a biofilm. Biofilms are held together and protected by a matrix of excreted polymeric compounds called EPS (exopolysacchride). Biofilms provide a protective environment for microorganisms that exist within the biofilm mass and a level of immunity from antibiotic treatments, except in doses that would be fatal to the patient. Consequently, biofilm microorganisms are not affected by the body's own infection-resistance mechanisms. In addition, bacterial biofilms may impair cutaneous wound healing and reduce topical antibacterial efficiency in healing or treating infected skin wounds.

Hypochlorous acid (HOCl) is an active component found in the human in system as a natural defense against infection, and thus kills bacteria, fungi and viruses without creating mechanisms for drug resistance. Hypochlorous acid compounds can be a safe, fast acting, broad spectrum antimicrobial for topical application, effective against all groups of hydrophobic, hydrophilic, gram-negative and gram-positive bacteria, and yeast, including *Pseudomonas*

*aeruginosa, Staphylococcus aureus*, and multi-drug resistant organisms like methicillin resistant *Staphylococcus aureus* (MRSA), and vancomycin resistant enterococci (VRE). In addition, hypochlorous acid compounds rapidly penetrate and disrupt biofilm and eradicate the pathogens, the major factor that inhibits wound healing. Unlike most antibiotics, which can take many hours to work, hypochlorous acid compounds, even at small doses, can help eradicate bacteria, fungi and viruses in minutes. When applied topically within a wound environment, hypochlorous acid compounds imme-diately disrupt and eradicate the bio-film, which surrounds and deactivates a broad spectrum of pathogenic microor-ganisms. Hypochlorous acid generally controls the tissue bacterial bio-burden without inhibiting the wound healing process and is also commonly associated with improved wound closure. Accordingly, a wound treatment therapy using a stabilized hypochlorous acid compound has recently been disclosed in U.S. Patent Publication No. 2012/0326680, the entirety of which is hereby incorporated by reference.

What is needed, then, is an apparatus that can effectively, and at low cost, operate in multiple treatment modes to deliver one or more different wound therapies to a wound site.

Disclosure of the Invention

In various embodiments, the wound treatment apparatus of the present invention may provide, using a unitary por-table device, both negative pressure wound therapy and positive pressure (hyperbaric oxygen) wound therapy to a wound site.

In one embodiment of the invention, the wound treatment apparatus includes a portable housing with a carry handle. A wound exudate container may be supported on the housing. A positive pressure device, e.g., a compressor pump, is disposed within the housing and is configured so that it can be fluidly coupled to an external source of oxygen and to an external wound dressing. The compressor pump delivers therapeutically effective levels of hyperbaric oxygen as a primary wound treatment fluid to the wound dressing during a first wound treatment mode. A negative pressure device, e.g. a vacuum pump, is also disposed within the housing and is configured for fluid coupling to the external wound dressing. The vacuum pump creates therapeutically effective levels of negative pressure to the wound dressing during a second wound treatment mode. A controller is disposed within the housing and operatively connected to the com-pressor pump and to the vacuum pump. A user interface is provided on the housing to communicate with the controller. The controller switches the apparatus between the first wound treatment mode and the second wound treatment mode. An oxygen concentrator may also be disposed within the housing and operatively coupled to the compressor pump so that the oxygen concentrator may supply oxygen enriched air to the compressor pump.

In some embodiments of the invention, oxygen and vacuum accumulator valves may be operatively coupled to the controller. An oxygen accumulator may be fluidly coupled to the compressor pump via the oxygen accumulator valve. A vacuum accumulator may be fluidly coupled to the vacuum pump via the vacuum accumulator valve. In such embodiments, the controller may be further configured to selectively actuate the oxygen and vacuum accumulator valves to facilitate application of positive and negative pressures at the wound dressing when the apparatus is transitioning between the first and second wound treatment modes.

According to another aspect of the invention, the appa-ratus may include a supplemental fluid delivery system in the housing, including at least one supplemental fluid vial adapted to contain a supplemental wound treatment fluid, such as an antiseptic, a medication, or hypochlorous acid. In such embodiments, the controller may be further configured to cause the supplemental fluid delivery system to deliver the supplemental wound treatment fluid to the wound dress-ing during the first wound treatment mode.

In a further aspect, the apparatus of the present invention may have a self-sterilization system, e.g., an ozone generator disposed within the housing. The self-sterilization system is responsive to the controller to selectively circulate steriliz-ing fluid, e.g. ozone, through the compressor pump and vacuum pump during a self-sterilization mode.

According to yet another aspect of the invention, an exudate safety system may be disposed within the housing. The exudate safety system may include a first pressure sensor to measure fluid pressures inside a wound treatment fluid output line, a second pressure sensor to measure fluid pressures inside a vacuum return line, and logic unit respon-sive to the first and second pressure sensors to determine and indicate exudate contamination of the apparatus.

Some embodiments of the apparatus may include a blood detection system disposed within the housing. The blood detection system includes at least one blood detection sensor that is functional to detect blood in exudate drawn from the wound dressing during the second wound treatment mode.

The above described features and advantages, as well as others, will become more readily apparent to those of ordinary skill in the art by reference to the following detailed description and accompanying drawings.

BRIEF DESCRIPTION OF THE DRAWINGS

The present invention may take form in various system and method components and arrangement of system and method components. The drawings are only for purposes of illustrating exemplary embodiments and are not to be con-strued as limiting the invention. The drawings illustrate the present invention, in which:

FIG. 6 is a simplified schematic of an embodiment of a blood detection system;

FIG. 7 is a simplified schematic of a second embodiment of a blood detection system.

FIG. 8 is a simplified schematic of a third embodiment of a blood detection system.

BEST MODE FOR CARRYING OUT THE INVENTION

Figure 1:
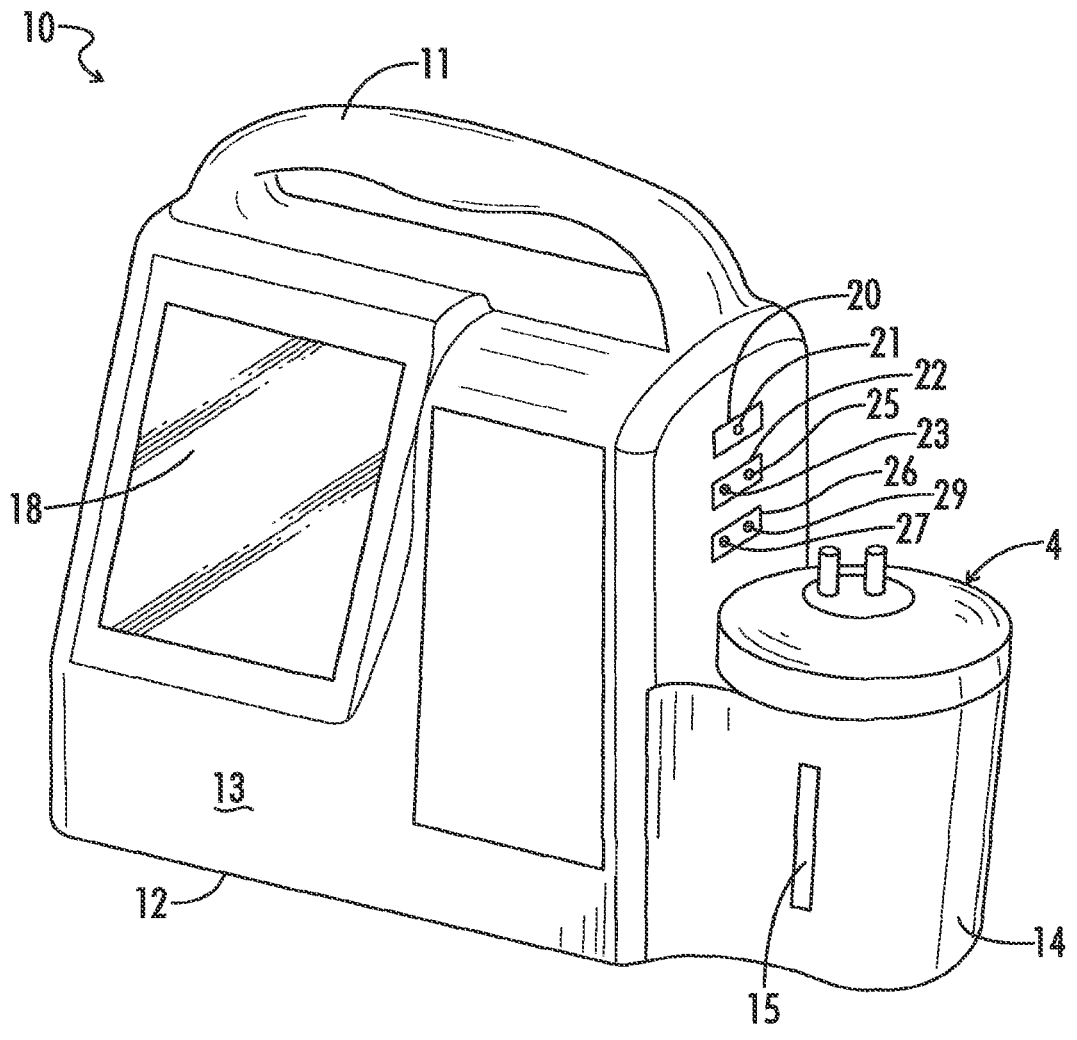
FIG. 1 is a perspective view of an embodiment of the apparatus of this invention.

Referring now to the drawings, FIGS. 1-8 illustrate an embodiment of the wound treatment apparatus of the present invention, which is designated generally as reference numeral 10. In an embodiment, wound treatment apparatus 10 is configured to provide both negative pressure wound treatment and positive pressure (e.g., hyperbaric oxygen) wound treatment to a wound site. The wound site may be covered by a wound dressing 6 (FIG. 2) that hermetically seals the wound site and facilitates the wound treatment. For example, the negative pressure and hyperbaric oxygen therapies may be delivered at therapeutic levels via a wound dressing using one or more operational in modes.

Therapeutically effective levels of hyperbaric oxygen and negative pressure treatments may be affected by different combinations of fluid pressures, fluid concentrations, fluid flow rates, treatment durations, and treatment intervals, as is known in the art. For example, in some embodiments of the present invention, therapeutically effective wound treatment levels and wound treatment protocols can be determined generally in accordance with the methods and principles and described in U.S. Pat. Nos. 7,648,488, 8,357,130, U.S. Patent Publication No. 2008/0140029, and U.S. Patent Publication No. 2010/0121287, all of which are hereby incorporated in their entirety by reference.

An example of a wound treatment protocol combining the application of negative pressure and hyperbaric oxygen treatments can include administering hyperbaric oxygen therapy to the wound in a range of approximately 8 minutes to approximately 12 minutes and administering negative pressure therapy to the wound at less than 1 atmosphere for approximately 8 minutes to approximately 12 minutes. However, the wound treatment cycle times and ranges may vary according to the nature and severity of the wound being treated and according to the wound response to the treatment. The hyperbaric oxygen therapy and the negative pressure therapy are administered intermittently such that negative pressure therapy is administered immediately following the administration of hyperbaric oxygen therapy and hyperbaric oxygen therapy is administered immediately following the administration of negative pressure therapy. In this exemplar wound treatment protocol, the wound may be subject to an absolute pressure of from approximately 60 mmHg to approximately 160 mm Hg during the administration of negative pressure therapy. Administering hyperbaric oxygen therapy may include supplying oxygen or humidified oxygen to the wound at a flow rate of approximately 0.1 liters per minute to approximately 3 liters per minute.

As shown in FIG. 1, an embodiment of the wound treatment apparatus 10 of the present invention may include a main unit body or housing 12 including a housing wall 13 that supports and encloses a variety of internal components within the device interior. The housing 12 is preferably provided with exterior dimensions and geometry to facilitate portability of the apparatus 10, including for example an integral or, attached carrying handle 11. Housing 12 may further include a user interface 18 integrated in, or attached to the exterior wall 13 of the housing 12. The interface 18 allows a user of the apparatus to monitor and set the various operational modes of the apparatus. In some embodiments, the user interface 18 may be a resistive or capacitive touch screen display, as generally known in the art, further having a smooth flat screen that is easily cleaned. In other embodiments, the user interface 18 may combine an LCD or other visual display screen with one or more user input devices, such as a key pad, touch pad, joy stick, switches, buttons, and toggles.

In some embodiments, a side pocket 14 may be attached to or integrally formed with housing wall 13. Side pocket 14 is preferably configured to receive and support a removable exudate canister 4. Side pocket 14 may further include an open or translucent vertical slot 15 in a wall of the pocket 14 so that fluid levels in exudate canister 4 may be visually monitored. Additional support pockets may be formed in or attached to the exterior of housing 12 to hold containers of hypochlorous acid or other supplemental wound treatment fluids, as described in more detail below.

In its various modes of operation, wound treatment apparatus 10 may fluidly communicate with wound dressing 6 and/or with external wound treatment fluid sources. To enable and accommodate this functionality, housing 12 may also be provided with separate lumen connectors or connector panels 20, 22 and 26, the purposes of which will be described more particularly below.

Figure 2:
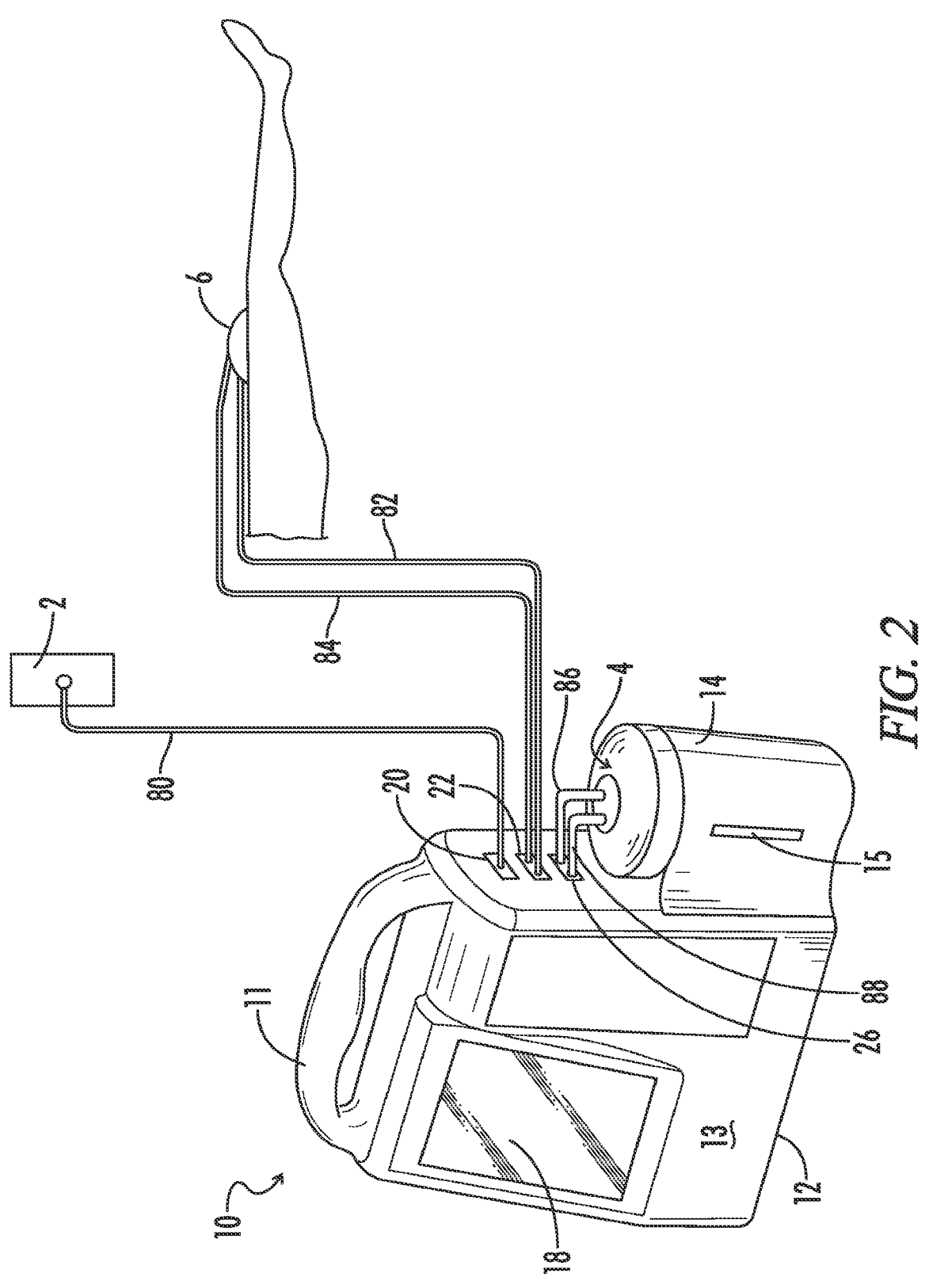
FIG. 2 is a perspective view of an embodiment of the apparatus connected to a wound dressing applied to a wound site and a removable exudate canister.

FIG. 2 shows apparatus 10 in a typical wound treatment application. In the embodiment as shown, various fluid transport lines or lumens 80, 82, 84, 86 and 88 respectively couple wound treatment apparatus 10 to an external source of a primary wound treatment fluid, e.g. oxygen supply source 2, to exudate canister 4, and to wound dressing 6.

In many embodiments and modes of operation, the external oxygen supply source 2 may be an external oxygen tank (not shown) or a wall-mounted oxygen port 2 connected to an in-house oxygen system.

Figure 3:
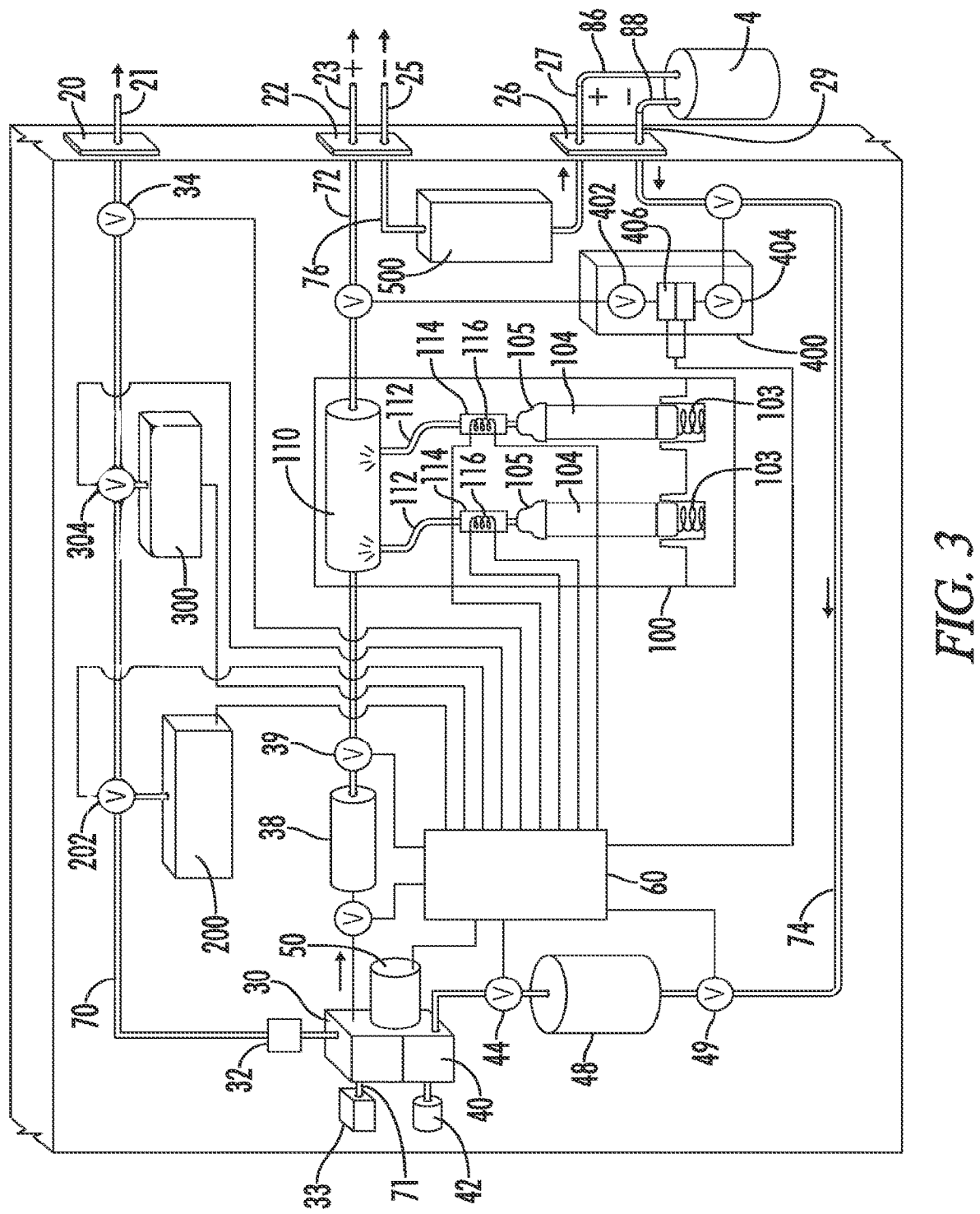
FIG. 3 is a simplified schematic of the internal compo-nents of the apparatus of FIG. 1.

Ideally, lumen connectors or connector panels 20, 22 and 26 each are attached to, formed in, or otherwise coupled to the housing wall 13 and have thru-wall fittings that are designed to ensure proper connection to their respective fluid lines or lumens 80, 82, 84, 86, and 88 between wound treatment apparatus 10 and oxygen source 2, exudate canister 4 and wound dressing 6. Thus, in the embodiment shown in FIGS. 2 and 3, oxygen supply connector 20 has a single oxygen supply fitting 21 (FIG. 3). An oxygen supply lumen 80 connects external oxygen supply 2 to oxygen supply fitting 21 of oxygen supply connector 20.

In the embodiment of FIGS. 2 and 3, wound treatment fluid connector 22 includes positive and negative pressure wound treatment fluid fittings 23 and 25. A positive pressure line or positive pressure wound treatment fluid lumen 82 connects wound dressing 6 to positive pressure wound treatment fluid fitting 23. A negative pressure line or negative pressure wound treatment fluid lumen 84 connects wound dressing 6 to negative pressure wound treatment fluid fitting 25.

As also shown in the embodiment of FIGS. 2 and 3, exudate connector 26 includes positive and negative pressure exudate fittings 27 and 29. Positive pressure exudate line or lumen 86 connects positive pressure exudate fitting 27 to removable exudate canister 4. Negative pressure exudate line or lumen 88 connects exudate canister 4 to negative pressure exudate fitting 29.

Referring now to FIG. 3, in some embodiments wound treatment apparatus 10 may include a negative pressure device and a positive pressure device configured inside housing 12. In some embodiments, the positive pressure device may be a compressor pump 30. The negative pressure device may be a vacuum pump 40.

In some embodiments, apparatus 10 may further include one or more of a supplemental fluid delivery system 100, an oxygen concentrator 200, a self-sterilization system 300, an exudate safety system 400, and a blood detection system 500, as further described below.

In some embodiments, compressor pump 30 may be of a conventional design suitable for use in medical applications, including being configured to provide a magnitude and duration of positive pressure at wound 6 that is effective for use in hyperbaric oxygen wound treatment. Vacuum pump
40 may also be of a conventional design suitable for medical
applications, including being configured to provide a mag-
nitude and duration of negative pressure that is effective for
use in negative pressure wound treatment.

Each pump 30 and 40 may be driven independently by its
own electrical motor or, as shown, separately driven by a
single electric motor 50. As shown, the input side of com-
pressor pump 30 may be fed by an oxygen source line 70
connected in fluid communication with oxygen supply fit-
ting 21 and alternatively by an ambient air source line 71
that is in open communication to the atmosphere outside
housing 18.

Oxygen source line 70 may include a filter 32 to keep dust
and other particulates from entering compressor pump 30
from the external oxygen source 2. Ambient air source line
71 may include a filter 33 to keep dust and other particulates
from entering compressor pump 30 from outside ambient air
drawn into the compressor pump 30. Oxygen source line 70
may further include an oxygen source valve 34, which
selectively opens and doses to control the supply of oxygen
from external oxygen source 2.

The output side of compressor pump 30 may be connected
to positive pressure wound treatment fluid fitting 23 of
wound treatment fluid connector 22 by wound treatment
fluid output line 72. Wound treatment fluid output line 72
may include a wound treatment fluid output valve 36 which
selectively opens and closes to control the supply of oxygen
under pressure to wound dressing 6.

In some embodiments, a vacuum return line 74 connects
negative pressure exudate fitting 29 of exudate connector 26
to the intake side of vacuum pump 40, Vacuum return line
74 may further include a vacuum return valve 44, which
selectively opens and closes to draw a vacuum pressure on
the wound site through exudate canister 4. A drainage loop
line 76 connects negative pressure wound treatment fluid
fitting 25 of wound treatment fluid connector 22 to positive
pressure exudate fitting 27 of exudate connector 26.

The outlet side of vacuum pump 40 may be connected to
a filter/muffler 42, to dampen pump noise and/or inhibit the
escape of exudate odors.

In an embodiment as shown in FIG. 3, compressor pump
30, vacuum pump 40, motor 50 and valves 36, 44, may be
functionally coupled (by direct electrical wiring or other
conventional electrical and/or fluid circuitry) to a logic unit
or controller 60. In some embodiments, various conven-
tional pressure and control sensors, relief valves, and control
valves (not shown) may also be coupled to the controller 60
and to one or more of the illustrated fluid lines, components,
and valves.

Wound treatment apparatus 10 may be electrically pow-
ered by any desirable means, such as an electrical AC grid
connection or internal battery cells and power packs for
portable convenience. Such power supplies are well known
in the electrical arts and readily applied for use in medical
device applications. In various embodiments, the controller
60 may have its own power supply or be connected to an
internal apparatus power supply (not shown).

Controller 60 may be an electromechanical controller, a
programmable logic controller, a microcontroller, a micro-
processor, or other controller of conventional design, as is
well know in the control arts. Controller 60 may be opera-
tively connected to the user interface 18 to receive com-
mands and/or to display information about the operation and
status of the apparatus 10.

Controller 60 may be programmed or otherwise config-
ured to monitor and control operation of the pumps, motor(s)

and other active components in apparatus 10, in particular,
controller 60 may be configured to cause apparatus 10 to
selectively operate in various modes, including a first wound
treatment mode (e.g. a positive pressure mode), a second
wound treatment mode (e.g. a negative pressure mode), a
transition mode, and a self-sterilization mode, as further
described below.

In some embodiments when operating in a first wound
treatment mode, or positive pressure mode, controller 60
actuates compressor pump 30 and opens valves 34 and 36 to
draw oxygen from the external oxygen source 2. Actuation
of compressor pump 30 further pushes oxygen into wound
dressing 6 at a positive pressure above atmospheric pressure,
via wound treatment fluid output line 72, positive pressure
wound treatment fluid fitting 23, and wound treatment fluid
supply lumen 82.

In some embodiments when operating in a second wound
treatment mode, or a negative pressure mode, controller 60
activates vacuum pump 40 and opens valve 44 to draw a
negative pressure within wound dressing 6 via negative
pressure wound treatment lumen 84, negative pressure
wound treatment fitting 25, and drainage loop line 76. This
draws exudate from the wound site 6 into exudate canister
4 via positive pressure exudate fitting 27 and positive
pressure exudate lumen 86.

In some embodiments, wound treatment apparatus 10
may operate in a temporary transition mode when changing
between the positive pressure mode and the negative pres-
sure mode. The transitional mode allows fluids in the various
lines and lumens to quickly clear and for pressures, both
negative and positive, to quickly build when switching
between the positive and negative pressure modes.

Wound treatment fluid output line 72 may, in some
embodiments, be fluidly coupled to compressor pump 30
through an oxygen accumulator system, including oxygen
accumulator 38 and associated oxygen accumulator valve
39. Vacuum return line 74 may be fluidly coupled to vacuum
pump 40 via a vacuum accumulator system including
vacuum accumulator 48 and an associated vacuum accumu-
lator valve 49. Oxygen accumulator 38 stores a volume of
oxygen under a positive pressure, while vacuum accumula-
tor 48 maintains its volume under a negative pressure. The
accumulation of positive and negative pressures may be
used to help expedite, e.g. accelerate, the pressurization of
wound dressing 6, both positively and negatively, when
transitioning between the negative and positive pressure
modes. Accumulators 38 and 48 may each have various
pressure sensors (not shown) and relief valves (not shown)
that are operatively coupled to controller 60, which monitors
and controls the pressure levels of the accumulators. Simi-
larly, valves 39 and 49 are also coupled to controller 60,
which is configured to control the actuation of both valves.

Supplemental Fluid Delivery System

Figure 4:
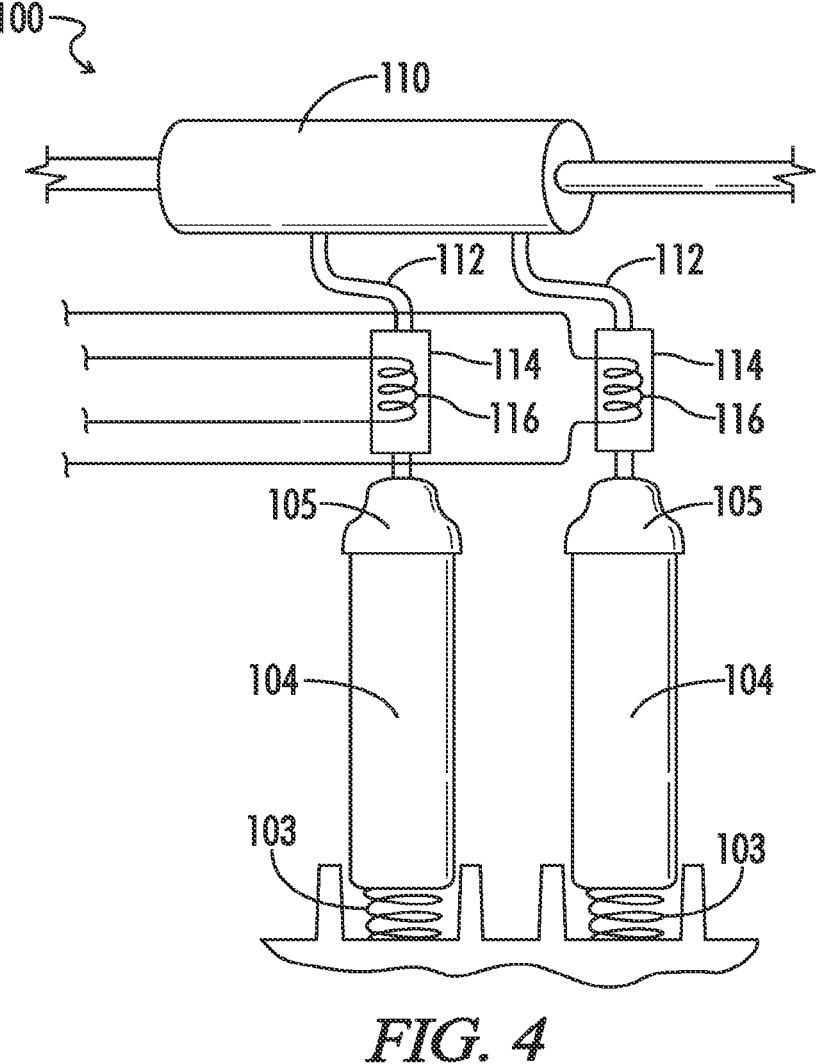
FIG. 4 is a simplified schematic of a supplemental fluid delivery system as shown in FIG. 3.

In various embodiments of apparatus 10, a supplemental
fluid delivery system 100 allows one or more supplemental
wound treatment fluids, such as hypochlorous acid, medi-
cations and disinfectants, to be introduced into the positive
pressure fluid flow and delivered to the wound site through
the wound dressing 6. Thus, as shown in FIGS. 3 and 4, the
internal components of supplemental fluid delivery system
100 may include a fluid manifold 110 in fluid communica-
tion with wound treatment fluid output line 72. One or more
supplemental fluid vials 104 may be coupled to manifold
110 through respective nozzles 105, controllable nozzle
fittings 114, and supplemental fluid lines 112. In some embodiments, the vials 104 may be internally pressurized using a propellant or externally pressurized using springs 103 biased against a movable floor of vials 104.

In other embodiments not shown, external vials or containers of supplemental wound treatment fluids may be provided and supported on the exterior of housing 12 and fluidly coupled to the internal components of the supplemental fluid delivery system 100.

A solenoid 116 may be configured inside each nozzle fitting 114 and electrically coupled to controller 60. The controller is programmed or otherwise configured to actuate one or more solenoids 116, causing its respective nozzle fitting 114 to depress nozzle 105 of a corresponding vial 104. This selectively meters the supplemental wound treatment fluids contained in vials 104 into manifold 110.

When the therapeutic fluids stored in vials 104 are dispersed into manifold 10 during the positive pressure operational mode, the flow of oxygen or air from compressor pump 30 carries the therapeutic fluids to wound dressing 6. While supplemental fluid delivery system 100 is illustrated and described using a solenoid actuated nozzle fitting used in conjunction with pressurized fluid vials, other actuation mechanisms and fluid containers may be employed within the teachings of the present invention.

Controller 60 may be programmed or otherwise configured to actuate supplemental fluid delivery system 100, so as to establish additional operational modes specific to desired fluid delivery wound treatment protocols. By way of example, wound treatment apparatus 10 may be configured via the user interface 18 and controller 60 to have an initial therapeutic operational mode where a first vial 104 containing an antiseptic fluid, such as hypochlorous acid or a saline solution, is delivered through hermetically sealed wound dressing 6 to flush the wound site. In an embodiment, this first delivery of a therapeutic fluid may be followed by a second therapeutic operational mode, where a second vial 104 containing a medicine, such as an antibiotic, is delivered through wound dressing 6 to the sealed wound site. Delivering therapeutic fluids directly to the wound site through wound dressing 6 may eliminate or reduce the need to remove the wound dressing 6 to apply localized or topical fluid treatments.

One example of a wound treatment protocol that includes the use of hypochlorous acid as a supplemental wound treatment fluid may include the use of a hydrophobic wound dressing, such as a dressing described in U.S. Pat. No. 4,617,326 and available from Abigo Medical AB under the Sorbact®. The hypochlorous acid compound may contain various stabilizers and other compounds to achieve the desired therapeutic properties.

Oxygen Concentrator

In certain embodiments, oxygen concentrator 200 acts as an internal oxygen and fluid supply source. In a particular embodiment, oxygen concentrator 200 may be of a type developed by Separation Design Group, TIC of Waynesburg, Pennsylvania, e.g., a self-contained modular device having a replaceable screw-in sieve bed that, when powered by a small compressor, can output 30 ml/minute of oxygen at 92% purity. In one aspect, oxygen concentrator 200 may a small, lightweight device that provides oxygen-enriched air using an ultra-rapid adsorption cycle based on advanced molecular sieve materials. Such devices are disclosed in U.S. Patent Publication No. 20120192864, the entirety of which is incorporated herein by reference.

For example, the module for the oxygen concentrator 200 may include a cartridge having a feed end and a product end, an input port for incoming air flow in the feed end, a feed end plug, a diffusion channel in the feed end, and an adsorbent bed contained the cartridge. The adsorbent bed will include a molecular sieve material having an average particle size of about 60.mu.m to 180.mu.m and having a substantially spherical shape and an aspect ratio of length to diameter of less than about 6. A fibrous pad may be positioned at one or both ends of the adsorbent bed. The module includes an output port for an oxygen-enriched product flow in the product end. A product end plug includes gas flow controls and at least one collection channel. The module further may include an enriched-oxygen product tube having an input end plug with an oxygen input port in the end plug and an output end plug having an oxygen output port in the output end plug. A product end block includes a passageway for transport of oxygen-enriched product with the cartridge and the enriched-oxygen product tube being connected to the product end block.

Oxygen concentrator 200 provides a supplemental fluid flow of oxygen enriched air when the apparatus 10 is operating in the positive pressure operational mode. Oxygen concentrator 200 generally provides sufficient oxygen and fluid flow to eliminate the need for an external oxygen source. As shown in the embodiment of FIG. 3, a valve 202 connects oxygen concentrator 200 to oxygen source line 70. Concentrator 200 and valve 202 may both be electrically connected or otherwise operatively coupled to controller 60, which controls the operation of the concentrator 200 and actuates the valve 202 to introduce oxygen provided from the concentrator 202 into oxygen source line 70.

Self-Sterilization System

In certain embodiments, a self-sterilization system 300 allows sterilization of all internal lines and components of wound treatment apparatus 10. The self-sterilization system 300 may include a source of a sterilization fluid, e.g. an ozone generator (not shown) operatively connected to oxygen source line 70 by a sterilizing fluid valve 304. The ozone generator may be of a conventional design and particularly selected to be light in weight and to have small footprint. Self-sterilization system 300 may also include a conventional ozone accumulator connected to the ozone generator for storing a volume of ozone to be used in the sterilization process. The ozone generator and valve 304 may both be electrically connected or otherwise operatively coupled to controller 60, which controls the operation of the generator and actuates the valve 304 to introduce ozone into oxygen source line 70. When the apparatus 10 is operating in a sterilization mode, compressor pump 30 circulates the ozone through the various pumps, accumulators, lines, valves, and fittings of wound treatment apparatus 10, thereby killing pathogens and microbes in the apparatus. In some embodiments, the various lumens 80, 82, 84, 86 and 88 are disconnected from wound treatment apparatus 10, connector fitting 21 is closed, and connector fittings 23 and 25, as well as connector fittings 27 and 29 are looped together using short sections of lumen or specialized connector loops (not shown) to close the fluid flow system before the sterilization mode is initiated. Controller 60 may be programmed or otherwise configured via the user interface 18 to initiate the sterilization mode as desired and clinically appropriate.

Exudate Safety System

Figure 5:
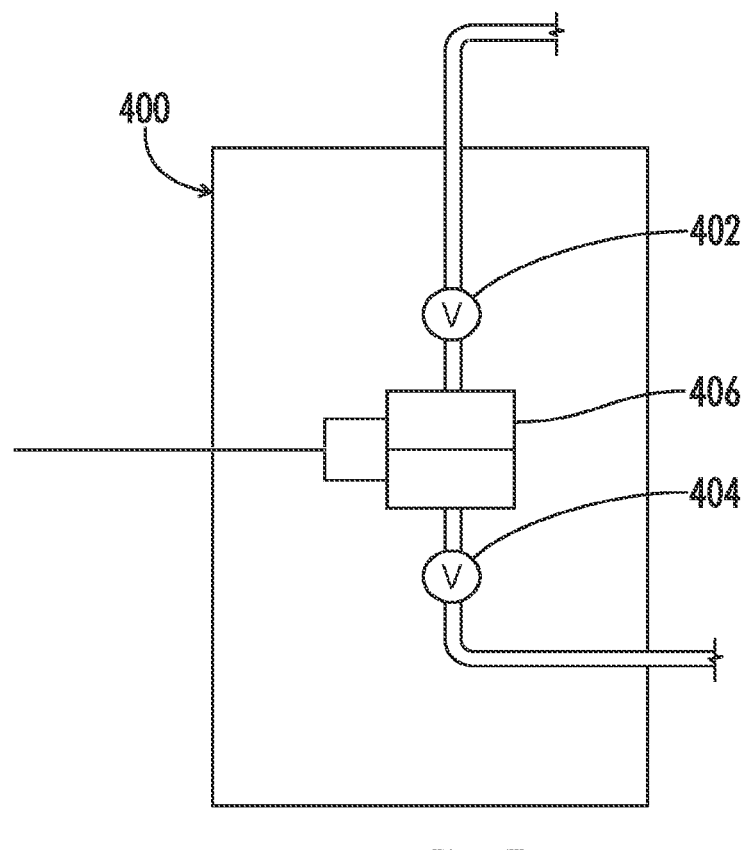
FIG. 5 is a simplified schematic of an embodiment of an exudate safety system.

In some embodiments of the apparatus 10, an exudate safety system 400 prevents exudate from contaminating wound treatment apparatus 10 by preventing exudate from entering and contaminating the apparatus. As shown in the embodiment of FIGS. 3 and 5, safety system 400 may include first and second pressure sensors or gauges 402 and 404 functionally coupled to a logic unit 406 that monitors pressure differentials between sensors 402 and 404. First sensor 402 senses a first device pressure, e.g. the pressure in wound treatment fluid output line 72. Second sensor 404 senses a second device pressure, e.g. the pressure in vacuum return line 74. Monitoring the pressure differential at these two (or other suitable) pressure sensing nodes can indicate that exudate may be from flowing back through wound dressing 6 and wound treatment fluid supply lumen 82 to contaminate portions of wound treatment apparatus 10.

In some embodiments, exudate safety system 400 may be functionally coupled to controller 60 so that alerts, alarms and interrupts can be triggered if an exudate contamination event cannot be inhibited or is detected. In other embodiments, controller 60 may be programmed or otherwise configured to respond to signals from logic unit 406. In response to these signals, and in particular in response to measured pressure differentials indicating a potential exudate contamination event, controller 60 can initiate adjustments at compressor pump 30, vacuum pump 40, and/or at one or more controllable apparatus valves to bring the sensed pressures back into a safe range to prevent contamination. In some embodiments, logic unit 406 may be integral with controller 60.

Blood Detection System in various embodiments of apparatus 10, a blood detection system 500 may be provided to monitor blood content within the exudate drawn from the wound site. As shown in the embodiment of FIG. 3, blood detection system 500 may be connected in fluid communication with drainage loop line 76 and further electrically connected or otherwise operatively coupled to controller 60. Blood detection system 500 monitors exudate drawn from wound dressing 6 for blood to ensure that at the wound site is not exacerbated bleeding during negative pressure treatment Blood detection system 500 may employ any variety of conventional methods and sensors for detecting the presence and level of blood in the exudate.

Examples of blood detection sensors usable in blood detection system 500 are illustrated in FIGS. 6-8. In the embodiment of FIG. 6, blood detection system 500 may employ one or more optical sensors 502 and related circuitry to provide a spectral (light and/or color) analysis of the exudate to detect the presence of blood. In another embodiment as shown in FIG. 7, blood detection system 500 may use circuitry 504 to directly or indirectly measure the capacitance or other electrical property of the exudate in relation to that of blood. In yet another embodiment as shown in FIG. 8, the blood detection system 500 may use sensors and circuitry 506 to measure the pH of the exudate to detect blood in the exudate (FIG. 6).

In various embodiments not shown, blood detection system 500 may further include an alarm or other device responsive to the blood detection sensor 502, 504, or 506 to provide a visible or audible signal that blood has been detected in the exudate. Alternatively, or in addition, the blood detection system 500 may be functionally coupled to controller 60 so that a blood detection event can be determined and signaled to a user of the apparatus 10 via user interface 18.

Different embodiments of the apparatus 10 may be portable and may combine a positive pressure source, a negative pressure source, a controller, and various combinations of the oxygen concentrator, supplement fluid delivery system, exudate safety system, self-sterilization system, and/or blood detection system.

In some embodiments of the apparatus, the controller 60 may include (or be coupled to) program memory that stores configuration and operational data that define and automatically implement the various operational modes and/or different wound treatment protocols as described above. In some embodiments, commands may be entered at the user interface 18 that define or modify operational modes and/or wound treatment protocols.

The embodiments of the present invention herein described and illustrated are not intended to be exhaustive or to limit the invention to the precise form disclosed. They are presented to explain the invention so that others skilled in the art might utilize its teachings. The embodiment of the present invention may be modified within the scope of the following claims.

We claim:

1. A portable wound treatment device comprising:
   a housing comprising an exterior wall enclosing a device interior, and a user interface panel arranged in the exterior wall;
   an oxygen supply connector panel coupled to the exterior wall and including at least one oxygen supply fitting extending through the exterior wall, the oxygen supply fitting configured to couple oxygen provided by an external oxygen source into the device interior;
   a wound treatment connector panel coupled to the exterior wall and including a positive pressure fitting and a negative pressure fitting, the positive pressure fitting configured to couple oxygen under positive pressure from the device interior to an external wound dressing, and the negative pressure fitting configured to apply a negative pressure from the device to the external wound dressing and to extract wound exudate from the external wound dressing into the device;
   a wound exudate connector panel coupled to the exterior wall and including a positive exudate fitting and a negative exudate fitting extending through the exterior wall, the positive exudate fitting configured to couple wound exudate from the negative pressure fitting to an exudate container, and the negative exudate fitting configured to provide a negative pressure to the exudate container;
   a positive pressure pump disposed in the device interior and coupled to the positive pressure fitting, the positive pressure pump effective to provide oxygen under positive pressure to the positive pressure fitting during a hyperbaric oxygen treatment mode;
   a negative pressure pump disposed in the device interior and coupled to the negative pressure fitting and to the negative exudate fitting, the negative pressure pump effective to provide negative pressure to the negative pressure fitting and to the negative exudate fitting during a negative pressure treatment mode;
   an oxygen concentrator disposed in the device interior and operatively coupled to the positive pressure pump, the oxygen concentrator effective to supply oxygen enriched air to the positive pressure pump during the hyperbaric oxygen treatment mode;
   a controller disposed in the device interior;
   an oxygen accumulator valve operatively coupled to the controller;

a vacuum accumulator valve operatively coupled to the controller;

an oxygen accumulator fluidly coupled to the compressor pump via the oxygen accumulator valve; and a vacuum accumulator fluidly coupled to the vacuum pump via the vacuum accumulator valve, wherein the controller is configured to selectively actuate the oxygen and vacuum accumulator valves to expedite application of positive and negative pressures at the external wound dressing during a transition mode between the positive and negative pressure operational modes.

2. The portable wound treatment device of claim 1 further comprising:

a supplemental fluid delivery system disposed within the device interior, the supplemental fluid delivery system operatively coupled to the controller and comprising a manifold configured to receive a supplemental wound treatment fluid and to deliver the supplemental wound treatment fluid to the positive pressure fitting; and the controller is further configured to cause the supplemental fluid delivery system to deliver the supplemental wound treatment fluid to the positive pressure fitting during the hyperbaric oxygen treatment mode.

3. The portable wound treatment device of claim 1 further comprising:

a self-sterilization system disposed within the device interior, the self-sterilization system operatively coupled to the controller and configured to receive a sterilizing fluid and to deliver the sterilizing fluid to the positive and negative pressure pumps; and the controller is further configured to cause the self-sterilization system to circulate the sterilizing fluid through the positive pressure pump and through the negative pressure pump during one or more device self-sterilization modes.

\* \* \* \* \*